United States Patent [19]

Chamberlin, Sr.

[11] Patent Number: Plant 6,008

[45] Date of Patent: Sep. 8, 1987

[54] PEACH TREE, "SEPTEMBER SUN"

[75] Inventor: Thomas O. Chamberlin, Sr., Visalia, Calif.

[73] Assignee: H. P. Metzler & Sons, Del Rey, Calif.

[21] Appl. No.: 786,829

[22] Filed: Oct. 11, 1985

[51] Int. Cl.[4] ..... A01H 5/00

[52] U.S. Cl. ..... Plt./43

[58] Field of Search ..... Plt./43

*Primary Examiner*—James R. Feyrer

*Attorney, Agent, or Firm*—Worrel & Worrel

[57] ABSTRACT

A new and distinct variety of peach tree which is characterized by fruit which is freestone in nature and has a flesh which is crisp and bright color having a skin which is of medium thickness and tenacious to flesh which makes the subject variety an exceptional peach to handle and ship.

1 Drawing Figure

BACKGROUND OF THE NEW VARIETY

The present invention relates to a new and distinct variety of peach tree denominated varietally as "September Sun", and more particularly to such a peach tree which bears a full freestone fruit which has a flesh which has a crisp texture and a bright yellow color, and which is further characterized as to novelty by a date of ripening of approximately August 30 through the first week of September and which has a skin of medium thickness which is tenacious to its flesh causing the subject variety to handle and to ship well.

From an economic standpoint, the relative dates of ripening of various varieties of peaches is of extreme importance. It has long been recognized as desirable to provide a peach tree that bears fruit later in the season than other varieties of peach trees which it most nearly resembles whereby the fruit can be sent to market at a time when competition is at a minimum. In addition, if the harvesting periods of various peaches can be effectively spread over a longer period of time, considerable savings and increased efficiency can be attained because the capitol expenditures required to harvest and transport such peaches can be spread over a longer period of time, resulting in lower cost of the final product and increasing the uniformity of production.

The new and distinct subject variety of peach tree is characterized as to novelty by producing a peach which matures for harvesting late in the season, approximately August 30 through the first week of September, at Del Rey, Calif., and in addition has a skin which is medium in thickness, and tenacious to flesh, making this particular peach particularly easy to handle and to ship to market.

ORIGIN AND ASEXUAL REPRODUCTION OF THE NEW VARIETY

The new and distinct variety of peach tree hereof was a chance seedling which was produced from the applicant's employer's Seed Lot Number 20, which is located in the H. P. Metzler & Sons nursery near Del Rey, Calif. The seed, which was of unknown parentage, was collected from the seedling block Number 20 in the fall of 1978. This chance seedling was then subsequently replanted in the H. P. Metzler & Sons nursery in the early spring of 1979. The new variety of peach tree produced its first fruit in the late summer of 1981. The superior characteristics of the subject variety were observed, recognized and appreciated by the applicant at that time and the seedling was marked for further observation and for asexual reproduction.

The applicant asexually reproduced the subject peach tree by removing budwood from the described chance seedling in the winter of 1981 and rebudding this particular budwood onto test seedlings in the early spring of 1982 in the H. P. Metzler & Sons test block which was located near Del Rey, Calif. This first propogation resulted in progeny being produced that were found to possess the same distinctive characteristics as the original seedling.

Inasmuch as the present variety was a chance seedling, its origin or cross is unknown although it was known by the applicant in the sense that he germinated the seed which produced the original seedling, asexually reproduced the seedling and tested the subject seedling at the designated nursery of the H. P. Metzler & Sons Company, of Del Rey, Calif.

BRIEF DESCRIPTION OF THE DRAWING

The accompanying drawing is a color photograph of a characteristic twig bearing typical leaves, which displays the dorsal and ventral coloration thereof, a cluster of two peaches showing their external coloration sufficiently matured for harvesting and shipment, three mature peaches of the color when matured on the trees, a peach halved transversely of the suture plane to illustrate the flesh coloration, and four stones, all of the subject variety.

DETAILED DESCRIPTION

Referring more specifically to the pomological details of this new and distinct variety of peach tree, the following has been observed under the ecological conditions prevailing at the nursery of the inventor's employer, H. P. Metzler & Sons of Del Rey, Calif. All major color code designations are by reference to the Inter-Society Color Council, National Bureau of Standards. Common color names are also used in several instances.

TREE

Size: Average.

Vigor: Extremely vigorous.

Productivity: Excellent.

Regularity of Bearing: Heavy, regular.

Trunk:
*Color.*—Dark Brown (62 d.g.y. Br.).
*Bark texture.*—Average peach bark.
*Lenticels.*—Approximately 7 to 8 per square inch.
Branches:
*Color.*—Dark Brown (62 d.g.y. Br.).
*Bark texture.*—Average peach bark.
*Lenticels.*—Approximately 7 to 8 per square inch.
*Lenticel size.*—Average in size.

LEAVES

Size:
*Average length.*—6½ inches to 7 inches, (165.7 mm through 177.8 mm).
*Width.*—1¾ inches to 2 inches, (44.45 mm through 50.8 mm).
Form:
*Marginal form.*—Serrate.
*Shape of leaf.*—Lanceolate.
Color:
*Dorsal side.*—127 gy. 0LG.
*Ventral side.*—122 gy. Y. G.
Petiole:
*Length.*—Approximately ½ inch, (12.7 mm).
*Thickness.*—Approximately ⅛ inch, (3.175 mm).
Stem glands:
*Number.*—Variable in number, normally 2, however 4 may occasionally be found.
*Arrangement.*—Generally arranged with two pairs being opposed, however some stems may be found that have only one pair at the base of the leaf.
*Size.*—Very small.
*Length.*—Approximately 1/32 inch to 1/16 inch (0.794 mm through 1.588 mm).
*Form of gland.*—Reniform.
*Color.*—107 m. 01.
Flower buds:
*Size.*—Diameter — approximately ¼ inch, (6.35 mm). Length — approximately 5/16 inch, (7.938 mm). Shape — slightly elongated; this shape is present before the red bud stage occurs.
*Color.*—Red and Green; Red — (12 s. Red); Green — (125 m 01.G).
*Color at red bud stage.*—A light Pink color appears at the Red bud stage, (250. m.p. Pk).
Flowers:
*Date of bloom.*—March 1 through March 5 at Del Rey, Calif.
*Size.*—Petal diameter — approximately 11/16 inch (17.462 mm). Petal length — approximately ¾ inch (19.05 mm).
*Color.*—Light Pink (249 L.P. Pk).
*Petal shape.*—Each petal appears almost round.
*General characteristics.*—The blossoms are large and quite attractive.

FRUIT

Maturity for harvest: Approximately August 30 to the first week in September at Del Rey, Calif.
Size:
*Diameter.*—2½ inches to 3½ inches, (63.5 through 88.9 mm).
*Uniformity.*—Good.
*Symmetry.*—Noteworthy.
*Diameter in the suture plane.*—2¾ inches to 3 inches, (69.85 through 76.2 mm).
*Diameter in the cheek plane.*—2¾ inches to 3 inches, (69.85 through 76.2 mm).
Form:
*Uniformity.*—Good.
*Symmetry.*—Noteworthy.
*Suture.*—Smooth and prominent.
*Length of suture.*—Approximately 4¼ inches, (107.95 mm).
*Position of suture.*—Suture extends from the base to the apex.
Ventral surfaces:
*Shape.*—Rounded and occasionally slightly flat.
Stem cavity:
*Shape of stem cavity.*—Rounded in appearance.
*Width of stem cavity.*—Approximately 1¼ inches, (31.75 mm).
*Depth of stem cavity.*—Approximately ½ inch (12.7 mm).
Base:
*Shape of base.*—Medium in width and flat in appearance.
Apex:
*Shape of apex.*—Rounded in shape and maybe slightly flat.
Pistil point:
*Shape of pistil point.*—Small in appearance, it may appear as though it is receded.
Stem:
*Length.*—Approximately 5/16 inch (7.938 mm).
*Width.*—Approximately ⅛ inch (3.175 mm).
Skin:
*Thickness.*—Medium in thickness.
*Texture.*—Very smooth.
*Tenacious to flesh.*—Yes.
*Tendency to crack.*—None observed.
*Color.*—Variable, from a very Dark Red to Bright Yellow; Red — (14 V. deep red); Yellow — (83 brill. yellow).
Flesh:
*Color.*—Yellow, (84 S. y).
*Surface texture of pit cavity.*—Rough, the flesh is very compact against the pit.
*Color of pit well.*—Dark Red, (13 Deep red).
*Aroma.*—Slight.
*Juice production.*—Average in juice production, no acid taste appears in the juice.
*Flavor of flesh.*—Good for a peach of such a late ripening date; the flavor is somewhat sweet.
*Fibers.*—None evident.
*Ripening.*—Even.
*Eating quality.*—Exceptional, firm, crisp and sweet.
Stone:
*Freestone or Clingstone.*—Freestone.
*Fibers.*—None evident.
*Size.*—Length — approximately 1-9/16 inches, (39.688 mm). Width — approximately 1 to 1⅛ inches, (25.4 through 28.575 mm). Thickness — approximately ¾ inch (19.050 mm).
*Form.*—The peach pit is not noteworthy in appearance.
*Appearance of ridges.*—The ridges of the subject variety pit are generally rough in appearance, and run generally on the longitudinal axis with the flat base. There is a slight ridge on both sides of the small apex point.
*Height of ridges.*—Approximately 1/16 inch (1.588 mm).
*Color of stone.*—Brown, (58 m. Br).

Use of peach: Fresh market.

Keeping quality: Exceptional; the subject variety has been kept in cold storage for three to four weeks with no deleterious effects noted.

Shipping quality: Exceptional, the subject variety ships well due to the thickness and tenacious nature of the skin.

Although the new variety of peach tree possesses the described characteristics as a result of the growing conditions prevailing in Del Rey, Calif., in the central part of the San Joaquin Valley, it is to be understood that variations of the usual magnitude in characteristics incident to growing conditions, fertilization, pruning and pest control are to be expected.

Having thus described my new variety of peach tree, what is new and desired to be secured by Letters Patent is:

1. A new and distinct variety of peach tree substantially as illustrated and described which produces peaches that are full freestone, which have flesh which is crisp and bright Yellow in color, which peaches are ripe for harvesting from August 30 through the first week of September, and which peaches further have skin of medium thickness, which is tenacious to the flesh of the instant variety, and causes fruit of the subject variety to display exceptional handling and shipping characteristics.

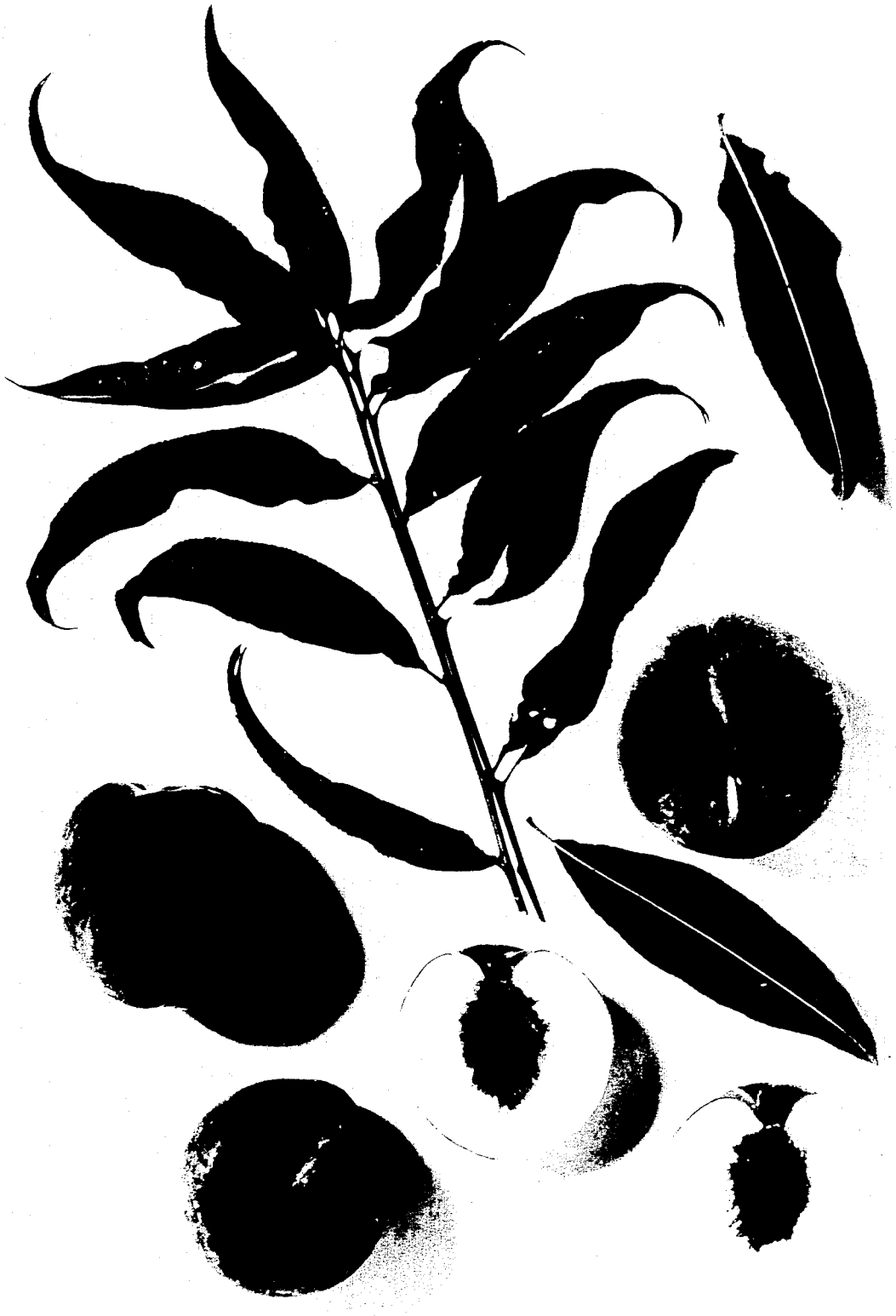

* * * * *